(12) United States Patent
Machida et al.

(10) Patent No.: US 11,350,894 B2
(45) Date of Patent: Jun. 7, 2022

(54) RADIATION IMAGING SYSTEM FOR ESTIMATING THICKNESS AND MIXING RATIO OF SUBSTANCES BASED ON AVERAGE PIXEL VALUE AND AVERAGE RADIATION QUANTUM ENERGY VALUE

(71) Applicant: CANON KABUSHIKI KAISHA, Tokyo (JP)

(72) Inventors: Yoshihito Machida, Sagamihara (JP); Atsushi Iwashita, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 629 days.

(21) Appl. No.: 15/771,058

(22) PCT Filed: Oct. 24, 2016

(86) PCT No.: PCT/JP2016/004671
§ 371 (c)(1),
(2) Date: Apr. 25, 2018

(87) PCT Pub. No.: WO2017/073043
PCT Pub. Date: May 4, 2017

(65) Prior Publication Data
US 2018/0325476 A1   Nov. 15, 2018

(30) Foreign Application Priority Data
Oct. 30, 2015 (JP) .............................. JP2015-215209

(51) Int. Cl.
*A61B 6/00* (2006.01)
*A61B 6/12* (2006.01)
(Continued)

(52) U.S. Cl.
CPC .......... *A61B 6/4241* (2013.01); *A61B 5/1075* (2013.01); *A61B 6/12* (2013.01);
(Continued)

(58) Field of Classification Search
CPC ....... A61B 6/4241; A61B 6/4283; A61B 6/12; A61B 6/5217; A61B 6/5205; A61B 6/482;
(Continued)

(56) References Cited

U.S. PATENT DOCUMENTS 6,233,473 B1   5/2001   Shepherd
7,725,153 B2   5/2010   Kelly
(Continued)

FOREIGN PATENT DOCUMENTS

CN   1509686 A   7/2004
CN   103796587 A   5/2014
(Continued)

*Primary Examiner* — Serkan Akar
*Assistant Examiner* — Richmond J Van Winter
(74) *Attorney, Agent, or Firm* — Canon U.S.A., Inc., IP Division

(57) ABSTRACT

A radiation imaging system includes a detector including a plurality of pixels which obtain pixel values corresponding to incident radiation transmitted through a subject, and an information processing unit configured to perform a process of estimating information on thicknesses of substances included in the subject using pixel values of an arbitrary one of the plurality of pixels, an average value of energy of radiation quanta of the arbitrary pixel calculated in accordance with the pixel values of the arbitrary pixel, a first table indicating the relationship between the pixel values of the arbitrary pixel and the thicknesses of the substances included in the subject, and a second table indicating the relationship between the average value of the energy of the radiation quanta of the arbitrary pixel and the thicknesses of the substances included in the subject.

13 Claims, 6 Drawing Sheets

(51) Int. Cl.
*A61B 5/107* (2006.01)
*G01T 7/00* (2006.01)
*G16H 50/30* (2018.01)

(52) U.S. Cl.
CPC .......... *A61B 6/4266* (2013.01); *A61B 6/4283* (2013.01); *A61B 6/481* (2013.01); *A61B 6/482* (2013.01); *A61B 6/505* (2013.01); *A61B 6/5205* (2013.01); *A61B 6/5217* (2013.01); *A61B 6/544* (2013.01); *A61B 6/563* (2013.01); *G01T 7/00* (2013.01)

(58) Field of Classification Search
CPC ....... A61B 6/4266; A61B 6/544; A61B 6/505; A61B 6/481; A61B 6/563; A61B 5/1075; G01T 7/00; G16H 50/30
See application file for complete search history.

(56) References Cited

U.S. PATENT DOCUMENTS

| | | | |
|---|---|---|---|
| 2003/0053597 A1* | 3/2003 | Flohr | G06T 11/006 378/156 |
| 2003/0133538 A1* | 7/2003 | Herve | A61B 6/482 378/53 |
| 2004/0028181 A1 | 2/2004 | Charles, Jr. | |
| 2008/0232668 A1* | 9/2008 | Kitamura | G06T 7/11 382/132 |
| 2009/0296884 A1 | 12/2009 | Honda | |
| 2011/0158386 A1 | 6/2011 | Payne | |
| 2013/0010927 A1* | 1/2013 | Seppi | A61B 6/032 378/86 |
| 2013/0121464 A1 | 5/2013 | Tajima | |
| 2013/0170614 A1 | 7/2013 | Yoshikawa | |
| 2013/0261443 A1* | 10/2013 | Machida | A61B 6/5205 600/431 |
| 2016/0354052 A1* | 12/2016 | Kawanishi | A61B 6/50 |

FOREIGN PATENT DOCUMENTS

| | | | |
|---|---|---|---|
| EP | 2649942 A1 | | 10/2013 |
| JP | H04-296064 A | | 10/1992 |
| JP | 2009-285356 A | | 12/2009 |
| JP | 2011-024773 A | | 2/2011 |
| JP | 2011024773 A | * | 2/2011 |
| JP | 2011024773 A | * | 10/2011 |
| JP | 2013-236962 A | | 11/2013 |
| JP | 2014-230584 A | | 12/2014 |
| WO | 03/103495 A1 | | 12/2003 |
| WO | 2015/046248 A1 | | 4/2015 |

* cited by examiner

FIG. 4A

|   | $d_1$ | $d_2$ | $d_3$ | $d_4$ | $d_5$ | $d_6$ |
|---|---|---|---|---|---|---|
| $\gamma_1$ | $i_1$ | $i_2$ | $i_2$ | $i_3$ | $i_4$ | $i_5$ |
| $\gamma_2$ | $i_1$ | $i_2$ | $i_2$ | $i_3$ | $i_4$ | $i_5$ |
| $\gamma_3$ | $i_1$ | $i_2$ | $i_2$ | $i_3$ | $i_4$ | $i_4$ |
| $\gamma_4$ | $i_1$ | $i_2$ | $i_2$ | $i_3$ | $i_4$ | $i_4$ |
| $\gamma_5$ | $i_1$ | $i_2$ | $i_2$ | $i_2$ | $i_3$ | $i_3$ |
| $\gamma_6$ | $i_1$ | $i_2$ | $i_2$ | $i_2$ | $i_3$ | $i_3$ |

|   | $d_1$ | $d_2$ | $d_3$ | $d_4$ | $d_5$ | $d_6$ |
|---|---|---|---|---|---|---|
| $\gamma_1$ | $e_5$ | $e_4$ | $e_3$ | $e_3$ | $e_2$ | $e_1$ |
| $\gamma_2$ | $e_5$ | $e_4$ | $e_4$ | $e_3$ | $e_2$ | $e_1$ |
| $\gamma_3$ | $e_5$ | $e_4$ | $e_4$ | $e_3$ | $e_2$ | $e_2$ |
| $\gamma_4$ | $e_5$ | $e_4$ | $e_4$ | $e_4$ | $e_3$ | $e_2$ |
| $\gamma_5$ | $e_5$ | $e_4$ | $e_4$ | $e_4$ | $e_3$ | $e_2$ |
| $\gamma_6$ | $e_5$ | $e_5$ | $e_4$ | $e_4$ | $e_3$ | $e_2$ |

402

RADIATION IMAGING SYSTEM FOR ESTIMATING THICKNESS AND MIXING RATIO OF SUBSTANCES BASED ON AVERAGE PIXEL VALUE AND AVERAGE RADIATION QUANTUM ENERGY VALUE

CROSS-REFERENCE TO RELATED APPLICATIONS

This application is a National Stage filing of International Application No. PCT/JP2016/004671 filed Oct. 24, 2016, which claims the benefit of Japanese Patent Application No. 2015-215209, filed Oct. 30, 2015, the disclosures of each of which are hereby incorporated by reference herein in their entirety.

TECHNICAL FIELD

The present invention relates to a radiation imaging system, an information processing apparatus which processes a radiation image, an information processing method for processing a radiation image, and a program.

BACKGROUND ART

As an imaging apparatus used for a medical image diagnosis and a non-destructive inspection using radiation (X-rays), a radiation imaging apparatus using a flat panel detector (FPD) formed of semiconductor material has been used. Such a radiation imaging apparatus may be used as a digital imaging apparatus which captures still images and moving images in the medical image diagnosis, for example.

Examples of the FPD include an integral sensor and a photon counting sensor. The integral sensor measures a total amount of charge generated by incident radiation. The photon counting sensor discriminates energy (wavelengths) of incident radiation and counts the numbers of times the radiation is detected for individual energy levels. Specifically, since the photon counting sensor has energy resolution capability, the photon counting sensor is expected to be applied to discrimination of substances and generation of an image and measurement of bone density in a case where imaging is virtually performed with monoenergetic radiation. However, since the number of incident radiation quanta is large, a high operation speed is required for individually counting the radiation quanta. Accordingly, it is difficult to realize the photon counting sensor in an FPD having a large area.

Therefore, PTL 1 proposes a radiation imaging apparatus which realizes energy resolution capability by estimating the number of radiation quanta and an average value of energy using average image density information and distribution information of image density for each predetermined region. Specifically, PTL 1 discloses an information processing method for estimating the number of radiation quanta and an average value of the energy using average image density information and distribution information of image density for each predetermined region and obtaining two types of image information, that is, the number of radiation quanta and the average value of the energy of the radiation quanta. When the method disclosed in PTL 1 is employed, a sensor having energy resolution capability may be realized even in a case of a low operation speed when compared with the photon counting sensor.

On the other hand, PTL 2 discloses a technique of an energy subtraction method. When the energy subtraction method is employed, two images are obtained by irradiation of respective two types of energy and a difference process is performed on the two images which have been subjected to a desired calculation so that the images of two substances having different attenuation coefficients are generated in a discrimination manner. The energy subtraction method utilizes a phenomenon in which different substances have different attenuation coefficients indicating degrees of attenuation of radiation at times when the radiation passes through the substances and the attenuation coefficients depend on energy of the radiation. Furthermore, PTL 2 further discloses a technique of dual-energy X-ray absorptiometry method (a DEXA method) which is a technique of measuring bone density utilizing the same phenomenon. However, radiation imaging is performed twice using two types of energy in the energy subtraction method and the DEXA method disclosed in PTL 2. Therefore, there arise problems in that artifact is generated due to a movement of a subject while energy is switched and in that high speed switching of radiation energy is required. In terms of these problems, the processing method disclosed in PTL 1 is more advantageous since substances may be discriminated from each other by one radiation imaging using one type of energy.

CITATION LIST

Patent Literature

PTL 1: Japanese Patent Laid-Open No. 2009-285356
PTL 2: Japanese Patent Laid-Open No. 2013-236962

SUMMARY OF INVENTION

Technical Problem

However, PTL 1 does not disclose a method for obtaining information for discriminating two substances constituting a radiation image using two types of image information, that is, the obtained number of radiation quanta and the obtained average value of the energy the radiation quanta.

Solution to Problem

Accordingly, the present invention provides a technique of obtaining information for discriminating two substances included in a radiation image of a subject without performing imaging by changing radiation energy. A radiation imaging system according to the present invention includes a detector including a plurality of pixels which obtain pixel values corresponding to incident radiation transmitted through a subject, and an information processing unit configured to perform a process of estimating information on thicknesses of substances included in the subject using pixel values of an arbitrary one of the plurality of pixels, an average value of energy of radiation quanta of the arbitrary pixel calculated in accordance with the pixel values of the arbitrary pixel, a first table indicating the relationship between the pixel values of the arbitrary pixel and the thicknesses of the substances included in the subject, and a second table indicating the relationship between the average value of the energy of the radiation quanta of the arbitrary pixel and the thicknesses of the substances included in the subject. An information processing apparatus which processes a radiation image according to the present invention performs a process of estimating information on thicknesses of substances included in a subject using pixel values of an arbitrary one of a plurality of pixels which obtain pixel values corresponding to incident radiation transmitted through the subject, an average value of energy of radiation quanta of the arbitrary pixel calculated in accordance with the pixel values of the arbitrary pixel, a first table indicating the relationship between the pixel values of the arbitrary pixel and the thicknesses of the substances included in the subject, and a second table indicating the relationship between the average value of the energy of the radiation quanta of the arbitrary pixel and the thicknesses of the substances included in the subject. An information processing method for a radiation image according to the present invention includes performing a process of estimating information on thicknesses of substances included in a subject using pixel values of an arbitrary one of a plurality of pixels which obtain pixel values corresponding to incident radiation transmitted through the subject, an average value of energy of radiation quanta of the arbitrary pixel calculated in accordance with the pixel values of the arbitrary pixel, a first table indicating the relationship between the pixel values of the arbitrary pixel and the thicknesses of the substances included in the subject, and a second table indicating the relationship between the average value of the energy of the radiation quanta of the arbitrary pixel and the thicknesses of the substances included in the subject. A program that executes information processing on a radiation image according to the present invention causes a computer to perform a process of estimating information on thicknesses of substances included in a subject using pixel values of an arbitrary one of a plurality of pixels which obtain pixel values corresponding to incident radiation transmitted through the subject, an average value of energy of radiation quanta of the arbitrary pixel calculated in accordance with the pixel values of the arbitrary pixel, a first table indicating the relationship between the pixel values of the arbitrary pixel and the thicknesses of the substances included in the subject, and a second table indicating the relationship between the average value of the energy of the radiation quanta of the arbitrary pixel and the thicknesses of the substances included in the subject.

Advantageous Effects of Invention

According to the present invention, information for discriminating two substances included in a subject may be obtained without performing imaging by changing radiation energy.

Further features of the present invention will become apparent from the following description of exemplary embodiments with reference to the attached drawings.

BRIEF DESCRIPTION OF DRAWINGS

FIG. 4A is a table used by an estimation unit.

FIG. 4B is a table used by the estimation unit.

DESCRIPTION OF EMBODIMENTS

Hereinafter, embodiments of the present invention will be described in detail with reference to the accompanying drawings. Note that, in this specification, examples of radiation include, in addition to an α-ray, a β-ray, a γ-ray, and so on which are beams formed by particles (including photons) emitted due to radioactive decay, beams having energy substantially the same as that of the beams formed by particles, such as an X-ray, a particle ray, and a cosmic ray.

First Embodiment

Figure 1:
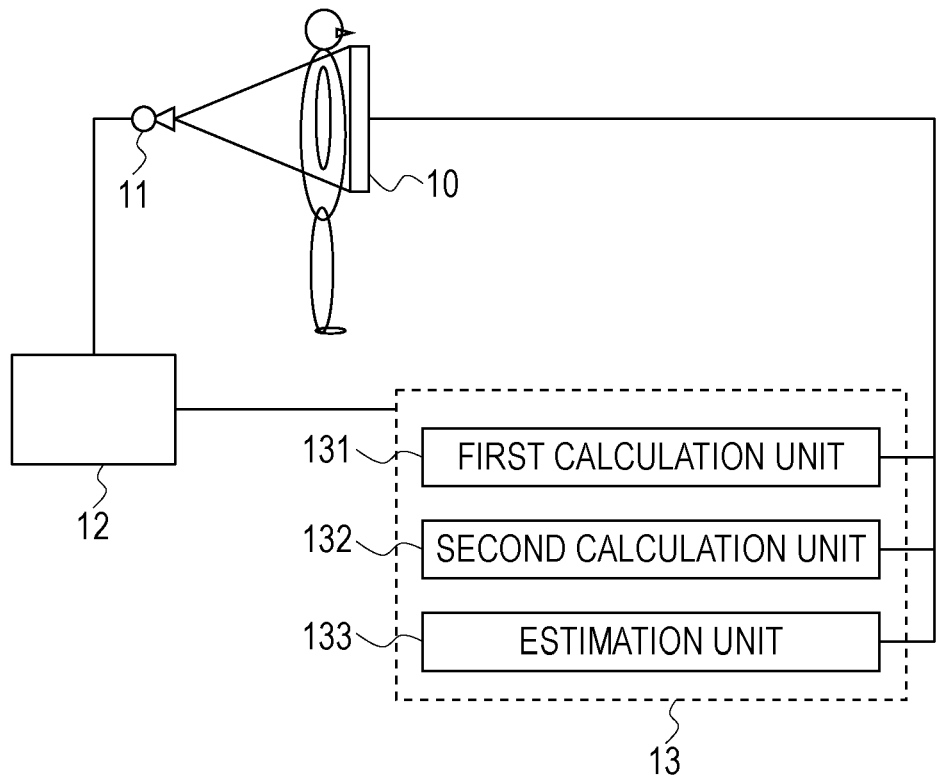
FIG. 1 is a diagram schematically illustrating a functional configuration of a radiation imaging system.
Figure 2:
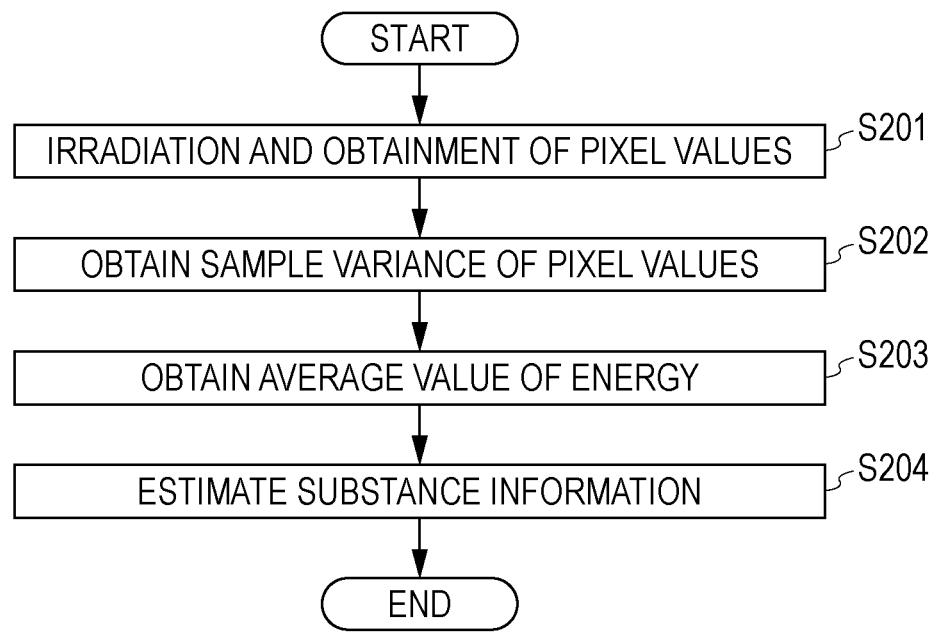
FIG. 2 is a flowchart illustrating a processing flow.

A configuration and a processing flow of a radiation imaging system according to a first embodiment will now be described with reference to FIGS. 1 and 2, respectively. FIG. 1 is a diagram schematically illustrating a functional configuration of the radiation imaging system according to the first embodiment. FIG. 2 is a flowchart illustrating a processing flow according to the first embodiment.

The radiation imaging system may include a radiation imaging apparatus 10, a computer 13, a radiation control apparatus 12, and a radiation generation apparatus 11. The radiation generation apparatus 11 emits radiation to a subject. The radiation imaging apparatus 10 includes a detector having a plurality of pixels which obtain pixel values corresponding to the radiation which enters through the subject. The detector obtains pixel values corresponding to the radiation which enters through the subject. The computer 13 serving as an image processing unit and/or an image processing apparatus of the present invention estimates an average value of energy of radiation quanta which reach the detector using the pixel values and further estimates information on thicknesses of substances constituting the subject. The estimation will be described in detail hereinafter. Furthermore, the computer 13 supplies control signals to the radiation imaging apparatus 10 and the radiation control apparatus 12 based on imaging information input by a photographer (not illustrated) through a control table (not illustrated) included in the computer 13. When receiving the control signal from the computer 13, the radiation control apparatus 12 controls an operation of emitting radiation from a radiation source (not illustrated) included in the radiation generation apparatus 11 and an operation of a irradiation field diaphragm mechanism (not illustrated). The detector of the radiation imaging apparatus 10 outputs an image signal corresponding to the radiation emitted from the radiation generation apparatus 11 controlled by the radiation control apparatus 12. The output image signal is transmitted to the computer 13 after being subjected to image processing, such as offset correction, performed by a signal processor. Here, a general wireless communication or a general wired communication is used in the transmission. The transmitted image signal is subjected to required image processing performed by the computer 13 before being displayed in a display unit (not illustrated) of the computer 13. Note that a pixel value constitutes a pixel signal.

The computer 13 includes, as a functional configuration thereof, a first calculation unit 131, a second calculation unit 132, and an estimation unit 133.

In step S201, radiation is emitted to the radiation imaging apparatus 10 through the subject for a predetermined period of time so that the computer 13 obtains a plurality of digital image signals.

Next, principle of calculations performed in step S202 and step S203 will be described. It is assumed here that the radiation emitted for the predetermined period of time is fixed and the subject does not move. An arbitrary one pixel is selected from among the obtained digital image signals. Although a digital signal (hereinafter referred to as a "pixel value") obtained from the selected pixel is ideally fixed, the pixel value varies in time series in practice. The variation includes quantum noise. The quantum noise is generated due to variation of the number of radiation quanta (the number of X-ray photons, for example) per unit time. If the variation of the number of radiation quanta is considered as occurrence probability of a discrete event per unit time, the variation of the number of radiation quanta is based on Poisson distribution which is discrete probability distribution having a specific random variable for counting discrete events generated at a given time interval. As for the Poisson distribution, when a random variable which has a value of a natural number satisfies a desired condition in a condition in which a constants λ is larger than 0, the random variable is based on the Poisson distribution of the parameter λ. Specifically, even in a case where images have the same average value of pixel values, distribution of the pixel values of one of the images formed by radiation quanta having larger energy is larger than that of the other image. By utilizing this, the energy of the radiation quanta, such as X-ray photons, may be estimated.

Hereinafter, a method for estimating energy of radiation quanta will be described using expressions. First, it is assumed that radiation is emitted to the radiation imaging apparatus 10 T times (T is a natural number equal to or larger than 2) so that T digital image signals are obtained by the radiation imaging apparatus 10. Here, assuming that a pixel value of a pixel of a t-th digital image signal (t is a natural number equal to or larger than 2 and equal to or smaller than T) is denoted by "I(t)", the total number of radiation quanta which have reached the pixel and absorbed by the pixel is denoted by "N", and an average value of the energy of the radiation quanta is denoted by "$E_{Ave}$", Expression (1) below is obtained.

$$E_{Ave} \times N = \Sigma I(t) \quad (1)$$

According to Expression (1), assuming that an arithmetic average of the numbers of radiation quanta which have reached and which have absorbed by the pixel of a single digital image signal is denoted by "$n_{Ave}$", Expression (2) below is obtained.

$$n_{Ave} = N/T = \Sigma I(t)/E_{Ave}/T \quad (2)$$

Furthermore, according to Expression (1), assuming that sample variance of the numbers of radiation quanta which have reached and which have absorbed by the pixel of the single digital image signal is denoted by "$n_{Var}$", Expression (3) below is obtained.

$$n_{Var} = \Sigma[\{I(t)/E_{Ave} - n_{Ave}\}^2]/T \quad (3)$$

Here, in the Poisson distribution, an expected value and variance are equal to the parameter λ. Furthermore, as the number of samples is increased, the arithmetic average becomes close to the expected value and the sample variance becomes close to the variance. Therefore, assuming that the number of samples is sufficiently large (preferably infinite) and the arithmetic average $n_{Ave}$ of the numbers of radiation quanta and the sample variance $n_{Var}$ of the numbers of radiation quanta are approximated so as to be equal to each other, Expression (4) is obtained since Expressions (2) and (3) are equal to each other.

$$E_{Ave} = \Sigma\{I(t)^2\}/\Sigma\{I(t)\} - \Sigma\{I(t)\}/T \quad (4)$$

In this way, an average value $E_{Ave}$ of the energy of the radiation quanta which have reached the pixel and which have been absorbed by the pixel is estimated and calculated using the pixel value I(t) of the pixel of the arbitrary t-th digital image signal.

Furthermore, assuming that the arithmetic average of the pixel values I(t) is denoted by "$I_{Ave}$", an arithmetic average $I_{Ave}$ is represented by Expression (5) below using the arithmetic average $n_{Ave}$ of the number of radiation quanta.

$$I_{Ave} = n_{Ave} \times E_{Ave} \quad (5)$$

Furthermore, assuming that sample variance of the pixel values is denoted by "$I_{Var}$", the sample variance $I_{Var}$ of the pixel values is represented by Expression (6) below using the sample variance $n_{Var}$ of the numbers of radiation quanta.

$$I_{Var} = n_{Var} \times E_{Ave}^2 \quad (6)$$

Accordingly, an average value E of the energy of the radiation quanta which have reached the pixel and which have absorbed by the pixel is also represented by Expression (7) below.

$$E_{Ave} = I_{Var}/I_{Ave} \quad (7)$$

In step S202, the first calculation unit 131 calculates the sample variance $I_{Var}$ of the pixel values of the arbitrary pixel using the pixel values I(t) of the arbitrary pixel in accordance with Expression (8) below. Although the sample variance is used as variance in this embodiment, unbiased variance may be used. Furthermore, although an arithmetic average $I_{Ave}$ of the pixel values I(t) is used as an average of pixel values, the present invention is not limited to this.

[Math. 1]

$$I_{var} = \frac{1}{T}\Sigma I(t)^2 - \left[\frac{1}{T}\Sigma I(t)\right]^2 \quad (8)$$

In step S203, the second calculation unit 132 calculates the average value $E_{Ave}$ of the energy of the radiation quanta of the arbitrary pixel using the sample variance $I_{Var}$ of the pixel values of the arbitrary pixel in accordance with Expression (9) below calculated using Expression (7). Here, α is an arbitrary constant used to perform conversion between a pixel value and a unit of energy. Although the sample variance is used as variance in this embodiment, unbiased variance may be used.

[Math. 2]

$$E_{Ave} = \alpha \frac{I_{var}}{I_{Ave}} \quad (9)$$

Figure 3:
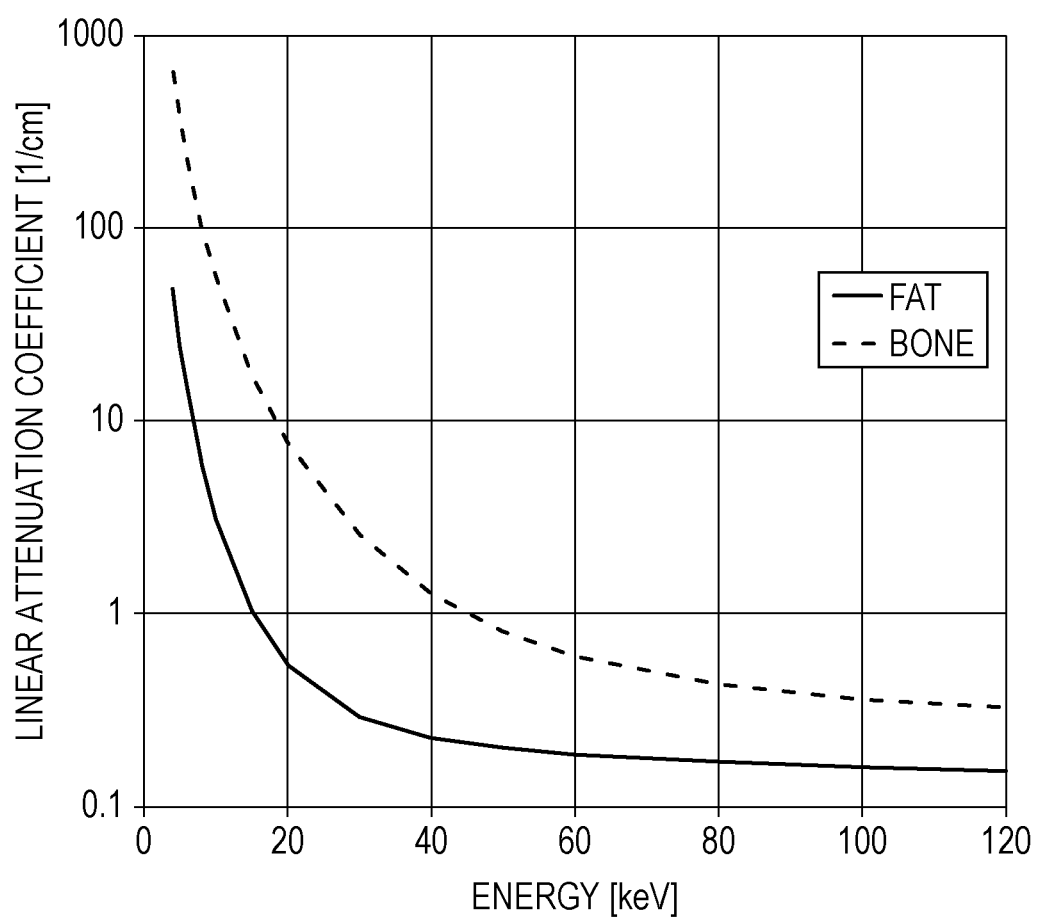
FIG. 3 is a graph illustrating linear attenuation coefficients of a bone and fat.

In the following steps, information on thicknesses of the substances which constitute the subject are estimated using the average value of the energy of the radiation quanta of the arbitrary pixel calculated in step S202 and step S203 and the pixel values of the arbitrary pixel. Note that, for simplicity of description, it is assumed that a substance (a second constitutive substance) other than a bone (a first constitutive substance) in the substances included in a human body serving as an example of the subject is fat. Note that the first and second constitutive substances are different from each other. Although the substances other than a bone include fat, muscle, internal organs, and water, these substances have linear attenuation coefficients similar to one another when compared with that of the bone. FIG. 3 is a graph illustrating linear attenuation coefficients of a bone and fat. Although description will be made using the linear attenuation coefficients of a bone and fat hereinafter, two arbitrary linear attenuation coefficients are used depending on diagnosis usage or constitutive substances of the subject.

In step S204, the estimation unit 133 estimates a thickness of the subject and a mix ratio of the substances included in the subject using the average value $E_{Ave}$ of the energy of the radiation quanta of the arbitrary pixel and the arithmetic average $I_{Ave}$ of the pixel values of the arbitrary pixel calculated using the pixel values of the arbitrary pixel. Here, the estimation unit 133 may estimate the thickness of the subject and the mix ratio of the substances included in the subject using a table illustrated in FIG. 4A. FIG. 4A is a first table indicating the relationship among a thickness d of the subject, a mix ratio γ of the substances included in the subject, and the arithmetic average $I_{Ave}$ of the pixel values of the arbitrary pixel. Note that, in a case where the mix ratio γ is 1, the subject is constituted only by bones (the first constitutive substance), whereas in a case where the mix ratio γ is 0, the subject is constituted only by fat (the second constitutive substance). The first table is preferably obtained by experiment in advance. The first table may be calculated in advance in accordance with Expression (10) below. It is assumed here that a mass attenuation coefficient of a bone at a time when the radiation energy is E[kev] is denoted by "$\mu_1(E)$", a linear attenuation coefficient of fat at a time when the radiation energy is E[kev] is denoted by "$\mu_2(E)$", a thickness of the subject is denoted by "d", and the mix ratio of the substances included in the subject is denoted by "γ". Furthermore, rates (energy spectra) of the numbers of radiation quanta of energy of radial rays before the radial rays pass the subject are denoted by "n(E)". In step S204, the estimation unit 133 performs a calculation using Expression (10) below so as to obtain the thickness d of the subject and the mix ratio γ. Here, "β" denotes an arbitrary coefficient used to convert energy into a pixel value.

[Math.3]

$$I_{Ave} = \beta \int_0^\infty n(E) e^{-\mu_1(E)d\gamma - \mu_2(E)d(1-\gamma)} E dE \quad (10)$$

Note that "n(E)" is preferably measured in advance using a commercially available spectrometer. Since a simple expression for obtaining an energy spectrum is publicly available, the energy spectrum may be calculated using the simple expression in accordance with conditions of a tube voltage, an additional filter, and the like at a time when radiation is emitted. Furthermore, "β" is determined based on characteristics of a scintillator used in the radiation imaging apparatus 10 and characteristics of a system gain.

The estimation unit 133 may estimate the thickness of the subject and the mix ratio of the substances included in the subject in accordance with a table illustrated in FIG. 4B. FIG. 4B is a second table indicating the relationship among the thickness d of the subject, the mix ratio γ of the substances included in the subject, and the average value $E_{Ave}$ of the energy of the radiation quanta of the arbitrary pixel. The second table is also preferably obtained by experiment in advance. The second table may be calculated in advance in accordance with. Expression (11) below.

[Math. 4]

$$E_{Ave} = \frac{I_{Ave}}{\beta \int_0^\infty n(E) e^{-\mu_1(E)d\gamma - \mu_2(E)d(1-\gamma)} dE} \quad (11)$$

The estimation unit 133 estimates thicknesses of the substances and the mix ratio of the substances included in the subject which satisfy the calculated average value $E_{Ave}$ of the energy of the radiation quanta of the arbitrary pixel and the calculated arithmetic average $I_{Ave}$ of the pixel values of the arbitrary pixel using the tables illustrated in FIGS. 4A and 4B.

Hereinafter, the estimation performed in a case where the arithmetic average $I_{Ave}$ of the pixel values of the arbitrary pixel calculated from the pixel values of the arbitrary pixel is $i_3$ of FIG. 4A and the calculated average value $E_{Ave}$ of the energy of the radiation quanta of the arbitrary pixel is $e_4$ of FIG. 4B will be described as an example. First, a combination of a thickness d of the subject and a mix ratio γ which satisfies $i_3$ is retrieved from the first table in FIG. 4A. In this case, such combinations which satisfy $i_3$ are included in a region 401. Thereafter, a combination of a thickness d of the subject and a mix ratio γ which satisfies $e_4$ is retrieved from the second table in FIG. 4B. In this case, such combinations which satisfy $e_4$ are included in a region 402. Finally, a combination of a thickness d of the subject and a mix ratio γ which satisfies both of the regions 401 and 402 is retrieved. In this case, a combination of a thickness $d_4$ of the subject and a mix ratio $\gamma_4$ satisfies both of the regions 401 and 402. As described above, since the two tables are used, the thickness of the subject and the mix ratio of the two substances included in the subject may be estimated. Although the tables have six rows and six columns as an example in this embodiment, larger tables are preferably used in practice. Furthermore, in a case where a plurality of results which satisfy both of the regions 401 and 402 are obtained in adjacent numerical values, a combination of the smallest thickness d and the smallest mix ratio γ is obtained taking influence of scattered radiation into consideration. In actual imaging, a pixel value may be larger than a normal value due to the influence of scattered radiation. Therefore, in the case where a plurality of results which satisfy both of the regions 401 and 402 are obtained in adjacent numerical values, a thickness d and a mix ratio γ which attain the largest calculated average value $E_{Ave}$ of the energy of the radiation quanta of the arbitrary pixel and the largest calculated arithmetic average $I_{Ave}$ of the pixel values of the arbitrary pixel are selected.

By performing the process from step S201 to step S204 described above, information on the thicknesses of the substances included in the subject and information on a component ratio may be estimated. According to this embodiment, the information on the thicknesses of the two different substances included in the subject and the information on the component ratio of the substances may be estimated without changing radiation energy in imaging. Accordingly, information for discriminating two substances included in a radiation image which may be applied to a complicated radiographic system in general imaging and fluorography may be obtained.

Although information on a bone and fat in a human body are estimated using the human body as the subject as an example in this embodiment, the present invention is not limited to this. For example, information on a contrast agent and a human body may be estimated so that visibility of distribution of the contrast agent is improved and an amount of the contrast agent to be used is reduced. Furthermore, information on a guide wire and a human body may be estimated so that visibility of the guide wire is improved, and accordingly, security of a patient during an operation may be ensured and a burden of a doctor during an operation may be reduced. In this way, information on a thickness and information on density of at least one of arbitrary different types of two substances may be obtained irrespective of a type of substance in the present invention.

Furthermore, a value BMD [g/cm$^2$] corresponding to bone density may be estimated by using density $\rho_1$ [g/cm$^3$] and a thickness d [cm] of the one and a mix ratio γ, for example.

Furthermore, although information on the thicknesses and the mix ratio of the substances included in the subject are estimated in this embodiment, the present invention is not limited to this. For example, if bone density and fat density may not be obtained or are unknown, the thicknesses d of the substances included in the subject may be multiplied by the density ρ so as to obtain a value ρd. For example, first information on a thickness and density of the first constitutive substance is represented by "$\rho_1 d_1$" and second information on a thickness and density of the second constitutive substance is represented by "$\rho_2 d_2$". Here, it is assumed that a mass attenuation coefficient of a bone obtained when radiation energy is denoted by "E[kev]" is denoted by "$\mu(E)_1$", a thickness of the bone is denoted by "$d_1$", and density of the bone is denoted by "$\rho_1$". In addition, it is assumed that a mass attenuation coefficient of fat obtained when radiation energy is denoted by "E[kev]" is denoted by "$\mu(E)_2$", a thickness of the fat is denoted by "$d_2$", and density of the fax is denoted by "$\rho_2$". The estimation unit 133 estimates an arithmetic average of the pixel values of the arbitrary pixel by performing calculation using Expression (12) below. Note that, although the arithmetic average $i_{Ave}$ of the pixel values I(t) is estimated as an average of the pixel values, the present invention is not limited to this.

[Math.5]

$$i_{Ave} = \beta \int_0^\infty n(E) e^{-\mu(E)_1 \rho_1 d_1 - \mu(E)_2 \rho_2 d_2} E dE \quad (12)$$

Furthermore, the estimation unit 133 estimates an average value $e_{Ave}$ of the energy of the radiation quanta of the arbitrary pixel by performing calculation using Expression (13) below. Note that, although the arithmetic average $i_{Ave}$ of the pixel values I(t) is estimated as an average of pixel values, the present invention is not limited to this.

[Math. 6]

$$e_{Ave} = \frac{i_{Ave}}{\beta \int_0^\infty n(E) e^{-\mu(E)_1 \rho_1 d_1 - \mu(E)_2 \rho_2 d_2} dE} \quad (13)$$

Then the estimation unit 133 uses "$\rho_1$" and "$i_{Ave}$" instead of "γ" and "$I_{Ave}$" of FIG. 4A and uses "$\rho_2$" and "$e_{Ave}$" instead of "γ" and "$E_{Ave}$" of FIG. 4B so as to estimate information on thicknesses and densities of the substances included in the subject. Specifically, in the present invention, the estimation unit 133 may use the first table indicating the relationship between the arithmetic average $I_{Ave}$ of the pixel values of the arbitrary pixel and the thicknesses d of the substances included in the subject for the estimation process. Furthermore, the estimation unit 133 may use the second table indicating the relationship between the calculated average value $E_{Ave}$ of the energy of the radiation quanta of the arbitrary pixel and the thicknesses d of the substances included in the subject for the estimation process. Then the estimation unit 133 estimates information on the thicknesses of the substances included in the subject using the arithmetic average $I_{Ave}$ of the pixel values of the arbitrary pixel, the arithmetic average $I_{Ave}$ of the pixel values of the arbitrary pixel, the first table, and the second table.

Furthermore, although the sample variance and the arithmetic average are calculated using a plurality of pixel values obtained in time series and an average value of the energy of the radiation quanta is estimated in this embodiment, the present invention is not limited to this. For example, a case of pixel values of an arbitrary one of a plurality of pixels arranged in two-dimensional space arrangement positions in a matrix having an X axis indicating columns and a Y axis indicating rows will be considered. In this case, the average value of the energy of the radiation quanta may be estimated after sample variance and an arithmetic average of the pixel values of the arbitrary pixel are calculated using pixel values of a plurality of surrounding pixels. By this, an energy image may be calculated from a single still image.

Furthermore, although the arithmetic average and the sample variance calculated using the pixel values of the arbitrary pixel are used to obtain the average value $E_{Ave}$ of the energy of the radiation quanta of this embodiment, the present invention is not limited to this. As described below, the average value of the energy of the radiation quanta is calculated based on the pixel values of the arbitrary pixel, and therefore, an amount of temporal and/or spatial change of a pixel value of the arbitrary pixel may be used for the calculation, for example.

In actual radiation imaging, the subject may move while a plurality of images are captured (or a plurality of digital image signals are obtained by a radiation imaging apparatus 10). This happens in a case where imaging of an organ having a motion, such as a heart, is performed, a case where fluoroscopic radiography is performed during an operation, and the like. If a subject has a motion, the number of X-ray photons which is an example of the number of radiation quanta which reach a certain pixel is changed while the radiation imaging apparatus 10 outputs a plurality of image data. Specifically, the parameter λ, of the Poisson distribution is changed. Accordingly, artifact is generated in an image generated using the average value of the energy, and therefore, diagnosis performance is degraded.

Therefore, it is preferable that the energy of the radiation quanta in the arbitrary pixel is estimated using an amount of temporal and/or spatial change of a pixel value of the arbitrary pixel when the average value of the energy of the radiation quanta in the arbitrary pixel is estimated. Here, the amount of temporal change of a pixel value means a difference between a pixel value of a pixel corresponding to (a pixel in a position the same as or in the vicinity of) the arbitrary pixel in a frame different from a frame in which the arbitrary pixel is specified and the pixel value of the arbitrary pixel. Furthermore, the amount of spatial change of a pixel value means a difference between a pixel value of a pixel positioned adjacent to or in the vicinity of the arbitrary pixel in the frame in which the arbitrary pixel is specified and the pixel value of the arbitrary pixel. The amount of temporal and spatial change means mix of the means described above. Note that the number of pixel values of the arbitrary pixel and the number of pixel values of a pixel which is compared with the arbitrary pixel may be single or plural. In a case of a plurality of pixels, a representative value of the pixels (for example, a value obtained by performing a recursive filter process or an averaging process on the values of the arbitrary pixel) is determined as the pixel value. Note that, although the different frame described above used when the amount of temporal change is to be obtained is preferably adjacent to the specific frame in a time axis, the different frame may be separated from the specific frame to a degree in which the effect is not degraded. Furthermore, although the arbitrary pixel and the different pixel are preferably adjacent to each other when the amount of spatial change is to be obtained, the pixels may be separated from each other to a degree in which the effect is not degraded. A range in which the effect is not degraded in despite of the separation is referred to as an arbitrary range which includes some of all pixel values used in signal processing. By using the change amount, error of the estimation of the average value of the energy of the arbitrary pixel may be suppressed.

More specifically, the present invention is based on a concept in which the sample variance of the pixel values is seen to be a half of square of the amount of temporal and/or spatial change of the pixel value of the arbitrary pixel and the energy of the radiation quantum in the arbitrary pixel is approximated. In particular, the present invention is based on a concept in which the sample variance of the pixel values is seen to be a half of square of a difference between the pixel value of the arbitrary pixel and the pixel value of the pixel in the position the same as the position of the arbitrary pixel in the different frame and the energy of the radiation quantum in the arbitrary pixel is approximated. Then averaging is performed using the approximated energy of the radiation quantum of the arbitrary pixel so that the average value of the energy of the radiation quantum of the arbitrary pixel is obtained. The energy of the radiation quantum in the arbitrary pixel has large error only when an expected value which is equal to the parameter λ of the Poisson distribution is changed. Accordingly, the generation of artifact may be suppressed.

Furthermore, the average value of the energy of the radiation quanta may be estimated using the energy of the radiation quanta obtained by counting the numbers of detection in a plurality of energy levels for each arbitrary pixel using a photon counting sensor as a detector, for example. In this case, the pixel value of the arbitrary pixel in the present invention may include a pixel value of an arbitrary pixel in the photon counting sensor.

Second Embodiment

Figure 5:
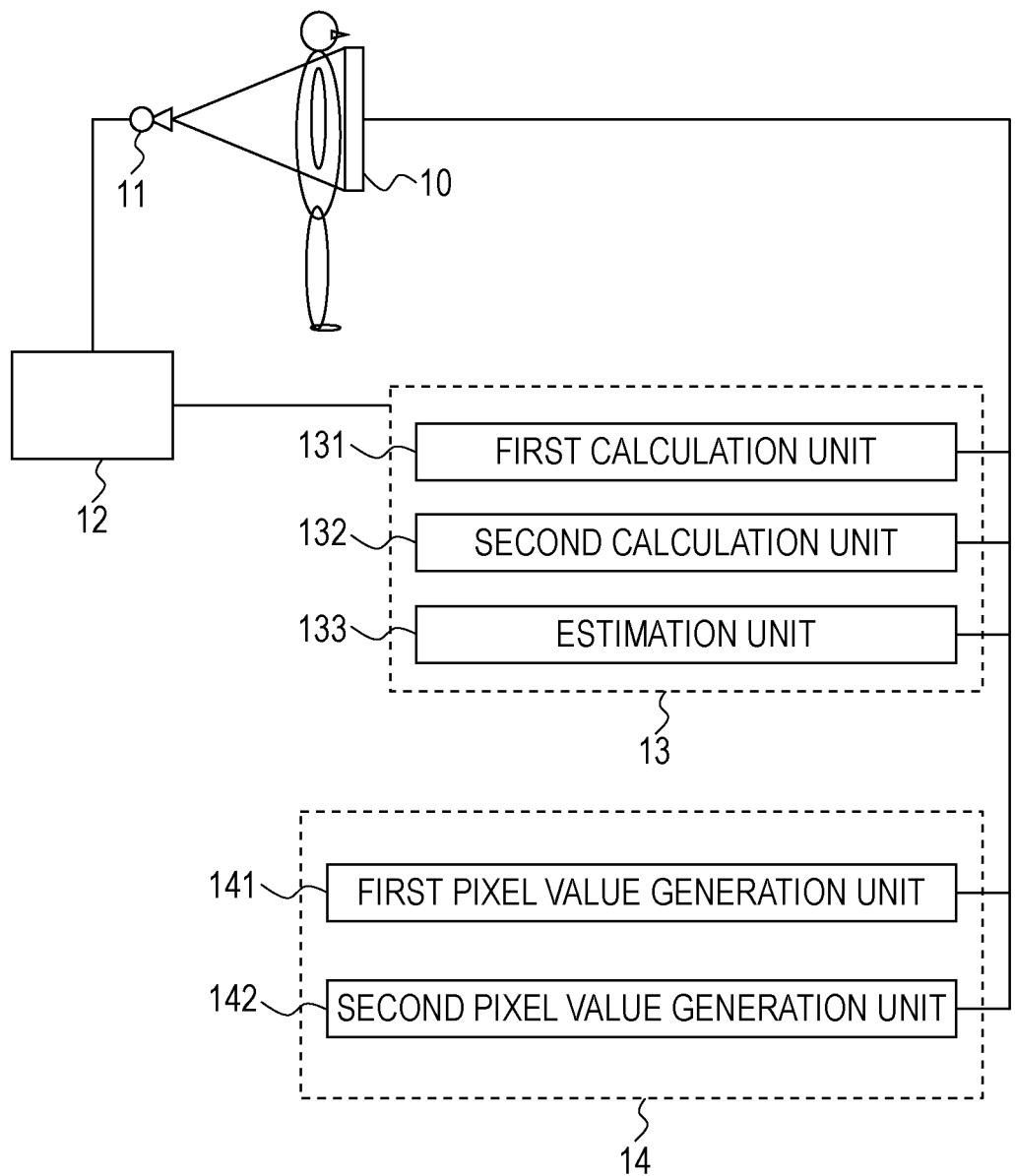
FIG. 5 is a diagram schematically illustrating a functional configuration of a radiation imaging system.
Figure 6:
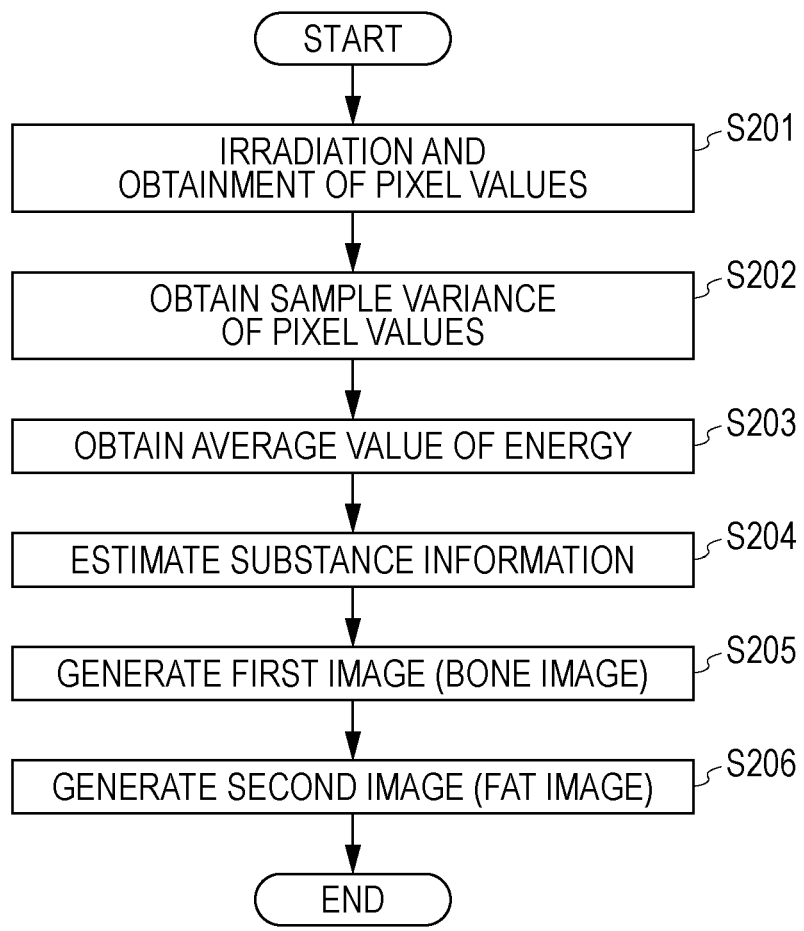
FIG. 6 is a flowchart illustrating a processing flow.

In a second embodiment, a method for generating pixel values of individual substances using information on thicknesses of the substances included in a subject obtained in the first embodiment will be described. Hereinafter, a method for generating an image of a human bone (a first constitutive substance) and an image of portions other than a bone in a discrimination manner will be described as an example with reference to FIGS. 5 and 6. FIG. 5 is a diagram schematically illustrating a functional configuration of a radiation imaging system according to the second embodiment. FIG. 6 is a flowchart illustrating a processing flow according to the second embodiment. Note that functional configurations and processing steps which are the same as those of the first embodiment are denoted by reference numerals the same as those of the first embodiment, and detailed descriptions thereof are omitted.

A pixel value generation unit 14 of FIG. 5 generates substance pixel values of the individual substances based on information on the thicknesses of the substances included in the subject and a mix ratio. The pixel value generation unit 14 includes a first pixel value generation unit 141 and a second pixel value generation unit 142. The first pixel value generation unit 141 generates a pixel value of a bone (a first pixel value) based on information on a thickness of the bone (the first constitutive substance) and a mix ratio (first information). The second pixel value generation unit 142 generates a pixel value of fat (a second pixel value) based on information on a thickness of the fat (the second constitutive substance) and a mix ratio (second information). Note that, for simplicity of description, as with the first embodiment, it is assumed that an image obtained by visualizing the substance other than the bone in the substances included in the substance is determined as a fat image. Although the substance other than the bone includes fat, muscle, internal organs, and water, these substances have linear attenuation coefficients similar to one another when compared with that of a bone.

In step S205 of FIG. 6, a pixel value (a first pixel value) $I_1$ of the bone is obtained using a calculation in accordance with Expression (14) below based on the first information obtained in the process from step S201 to step S204.

[Math.7]

$$I_1 = \beta \int_0^\infty n(E) e^{-\mu_1(E)d\gamma} E dE \tag{14}$$

In step S206, a pixel value (a second pixel value) $I_2$ of the fat is calculated using a calculation in accordance with Expression (15) below based on the second information obtained in the process from step S201 to step S204.

[Math.8]

$$I_2 = \beta \int_0^\infty n(E) e^{-\mu_2(E)d(1-\gamma)} E dE \tag{15}$$

By performing the process described above, substance pixel values of the individual two substances included in the subject may be generated.

Although the method for generating pixel values of the bone and the fat in the human body serving as the subject is described as an example in this embodiment, the present invention is not limited to this. For example, information on a contrast agent and a human body may be estimated so that visibility of distribution of the contrast agent is improved and an amount of the contrast agent to be used is reduced. Furthermore, if a pixel value of the contrast agent is generated, an image equivalent to a digital subtraction angiography image may be generated without capturing an image before the contrast agent is injected, and therefore, a relative positional change between a subject and a radiation imaging apparatus during photographing may be coped with. Furthermore, information on a guide wire and a human body may be estimated so that visibility of the guide wire is improved, and accordingly, security of a patient during an operation is ensured and a burden of a doctor during an operation is reduced. In this way, the pixel values of the two arbitrary types of substance may be generated irrespective of types of substance in the present invention. Furthermore, in a case where pixel values of all the two types of substance are not required, that is, in a case where only a pixel value of the bone is required or a case where only a pixel value of the contrast agent is required, a corresponding one of the processes in step S205 and step S206 may be omitted. Note that the pixel values obtained in Expressions (14) and (15) correspond to a pixel value obtained when only a bone is virtually captured and a pixel value obtained when only fat is virtually captured, respectively, by the radiation imaging apparatus.

Furthermore, the pixel values may be generated by performing calculations in accordance with Expression (16) and (17) below using an average (effective energy) $E_{eff}$ of energy spectra of emitted radiation.

[Math. 9]

$$I_1 = \beta e^{-\mu_1(E_{eff})d_1\gamma} \quad (16)$$

[Math. 10]

$$I_2 = \beta e^{-\mu_2(E_{eff})d_2(1-\gamma)} \quad (17)$$

In this way, the calculation may be simplified using the effective energy of the emitted radiation.

Furthermore, when arbitrary monochromatic radiation energy $E_{mono}$ is set, a pixel value of energy virtually having an arbitrary spectrum may be generated in accordance with a calculation of Expression (18) below.

[Math. 11]

$$I(E_{mono}) = \beta e^{-\mu_1(E_{mono})d_1\gamma - \mu_2(E_{mono})d_2(1-\gamma)} \quad (18)$$

It is assumed that a linear attenuation coefficient of an iodinated contrast agent is denoted by "$\mu_1$", a linear attenuation coefficient of the human body is denoted by "$\mu_2$", a thickness of the iodinated contrast agent is denoted by "$d_1$", a thickness of the human body is denoted by "$d_2$", and a mix ratio between the iodinated contrast agent and the human body is denoted by "$\gamma$", and contrast between the iodinated contrast agent and other substances is to be improved. In this case, since the iodinated contrast agent has a K absorption edge at 33.2 keV, the calculation is performed while arbitrary monochromatic radiation energy $E_{mono}$ of 33.2 keV is set.

Furthermore, the various pixel values may be generated by performing calculations in accordance with Expressions (19) and (20) below using an arithmetic average $I_{Ave}$ of pixel values based on obtained pixel values I(t).

[Math. 12]

$$I_1 = Ln(I_{Ave}) \frac{\mu_1(E_{eff})d\gamma}{\mu_1(E_{eff})d\gamma + \mu_2(E_{eff})d(1-\gamma)} \quad (19)$$

[Math. 13]

$$I_2 = Ln(I_{Ave}) \frac{\mu_2(E_{eff})d(1-\gamma)}{\mu_1(E_{eff})d + \mu_2(E_{eff})d(1-\gamma)} \quad (20)$$

Furthermore, obtained information $\mu_1 d\gamma$ may be set as a pixel value (a first pixel value) of a bone and obtained information $\mu_2 d(1-\gamma)$ may be set as a pixel value (a second pixel value) of fat. By displaying the value $\mu d\gamma$, degrees of attenuation of radiation in the individual substances may be visualized. For example, if bone density and fat density may not be obtained or are unknown, the thicknesses d of the substances included in the subject may be multiplied by the density $\rho$ so as to obtain a value $\rho d$ instead of $d\gamma$. It is assumed that first information on a thickness and density of the first constitutive substance is represented by "$\rho_1 d_1$" and second information on a thickness and density of the second constitutive substance is represented by "$\rho_2 d_2$". By displaying the value $\rho d$, area densities of the individual substances may be visualized. For example, "$\rho_1 d_1$" may visualize distribution of bone density. Furthermore, in a case where the bone density and fat density may be obtained or estimated by different methods, the individual thicknesses $d\gamma$ and $d(1-\gamma)$ may be determined as a pixel value of the bone (the first pixel value) and a pixel value of the fat (the second pixel value). In this way, two-dimensional distributions of the thicknesses of the individual substances may be visualized.

Hereinafter, a radiation imaging apparatus and a radiation imaging system which are suitable for obtaining pixel values to be used in the present invention will be described.

Figure 7:
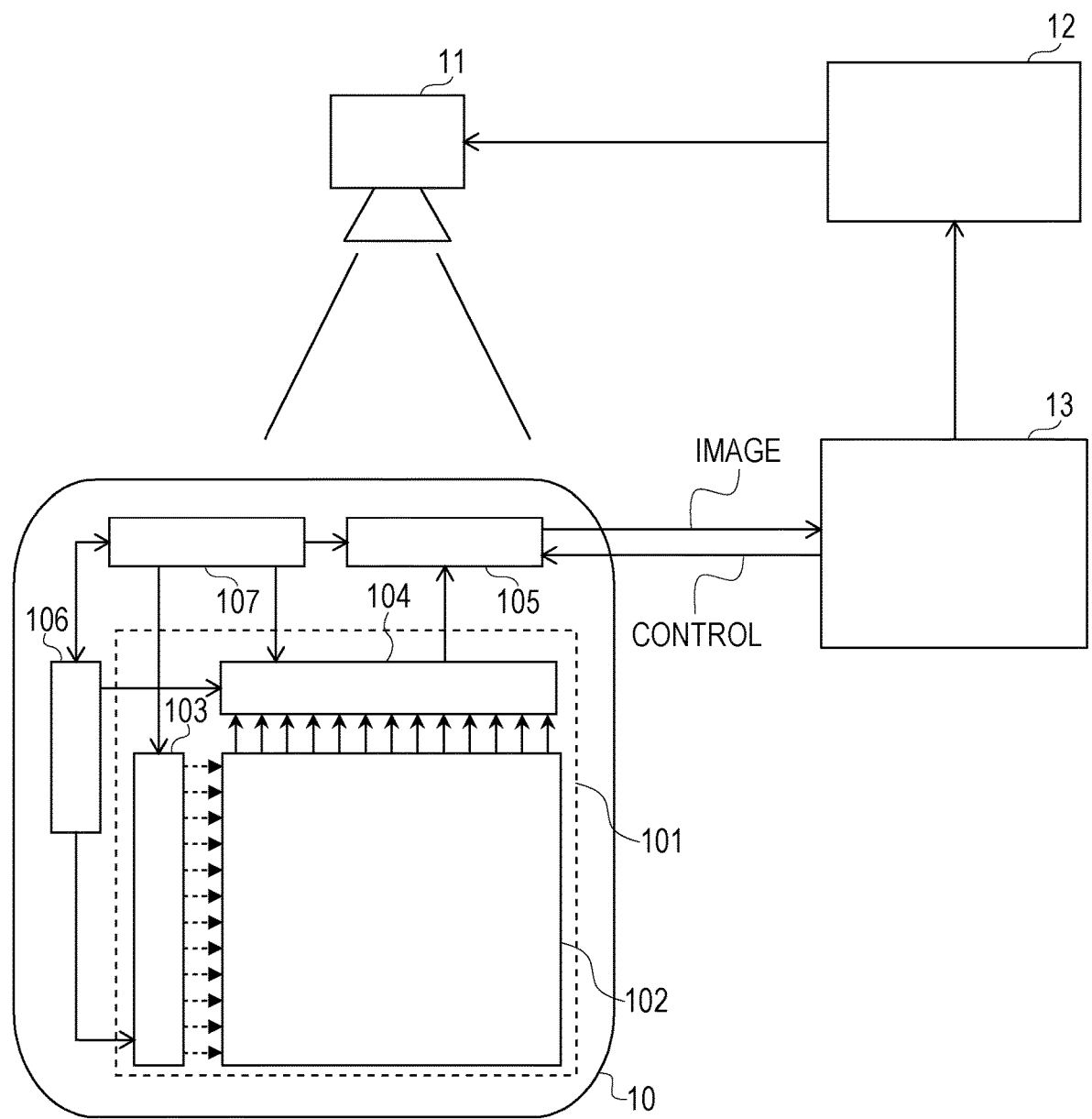
FIG. 7 is a block diagram schematically illustrating the radiation imaging system.

First, the radiation imaging system will be described with reference to FIG. 7. FIG. 7 is a block diagram schematically illustrating the radiation imaging system. Note that configurations the same as those illustrated in FIGS. 1 and 5 are denoted by reference numerals the same as those illustrated in FIGS. 1 and 5 in this embodiment, and detailed descriptions thereof are omitted.

A detector 101 may include a pixel array 102 including pixels in a matrix which convert radiation or light into electric signals, a driving circuit 103 which drives the pixel array 102, and an output circuit 104 which outputs the electric signals supplied from the driven pixel array 102 as image signals. The pixel array 102 includes the plurality of pixels which output electric signals corresponding to incident radiation so as to obtain pixel values corresponding to the radiation, and the plurality of pixels are preferably arranged in a matrix. Each of the plurality of pixels may include a photoelectric conversion element and a pixel circuit unit. The photoelectric conversion element converts light which has been converted from the radiation by a scintillator into charge, and a photodiode disposed on a semiconductor substrate, such as a silicon substrate, is used as the photoelectric conversion element. However, the present invention is not limited to this. A photoelectric conversion element of amorphous silicon disposed on an insulated substrate, such as a glass substrate, or a conversion element which directly converts radiation into charge without using a scintillator may be used, for example. A controller 107 of a radiation imaging apparatus 10 controls various units included in the radiation imaging apparatus 10 in response to control signals supplied from the computer 13. The detector 101 of the radiation imaging apparatus 10 outputs an image signal corresponding to the radiation emitted from the radiation generation apparatus 11 controlled by the radiation control apparatus 12. The output image signal is transmitted to the computer 13 after being subjected to image processing, such as offset correction, performed by a signal processor 105. Here, a general wireless communication or a general wired communication is used in the transmission. The transmitted image signal is subjected to required image processing performed by the computer 13 before being displayed in a display unit (not illustrated) of the computer 13.

Note that embodiments of a system, an apparatus, a method, a program or a storage medium, and the like may be employed in the present invention, for example. Specifically, the present invention may be applied to a system including a plurality of devices or an apparatus including a single device. Furthermore, although the processes described above are preferably performed in accordance with programs, all or some of the processes may be performed by a circuit. Alternatively, the processes may be performed by the signal processor 105 instead of the computer 13 or may be performed utilizing both of the signal processor 105 and the computer 13. That is, the information processing unit and/or the information processing apparatus according to the present invention corresponds to at least one of the signal processor 105, the computer 13, and a combination of the signal processor 105 and the computer 13.

The present invention is also realized by executing processing below. That is, software (programs) which realizes the functions of the foregoing embodiments is supplied to a system or an apparatus through a network or various storage media. Then a computer (or a CPU, an MPU, a CPU, or the like) included in the system or the apparatus reads and executes the programs.

Other Embodiments

Embodiments of the present invention can also be realized by a computer of a system or apparatus that reads out and executes computer executable instructions (e.g., one or more programs) recorded on a storage medium (which truly also be referred to more fully as a 'non-transitory computer-readable storage medium') to perform the functions of one or more of the above-described embodiments and/or that includes one or more circuits (e.g., application specific integrated circuit (ASIC)) for performing the functions of one or more of the above-described embodiments, and by a method performed by the computer of the system or apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-215209, filed Oct. 30, 2015, which is hereby incorporated by reference herein in its entirety.

REFERENCE SIGNS LIST

101 Detector
105 Signal processor
13 Computer

The invention claimed is:
1. A radiation imaging system comprising:
a detector including a plurality of pixels arranged in a matrix and acquiring pixel values corresponding to incident radiation transmitted through a subject corresponding to each of the plurality of pixels;
an estimation unit which estimates information on thicknesses and mixing ratio of substances included in the subject, the estimation unit having a first table indicating the relationship between the average value of the pixel values of an arbitrary pixel among the plurality of pixels, the thicknesses of the substances included in the subject, and the mixing ratio of the substances included in the subject, and a second table indicating the relationship between an average value of radiation quantum energy of the arbitrary pixel, the thicknesses of the substances included in the subject, and the mixing ratio of the substances included in the subject,
a first calculation unit for calculating an average value of pixel values of the arbitrary pixel,
a second calculation unit for calculating the average value of the radiation quantum energy of the arbitrary pixel on the basis of a variance value of pixel values of the arbitrary pixel and the average value of pixel values of the arbitrary pixel calculated by the first calculation unit, and
wherein the estimation unit estimates information on the thickness and the mixing ratio of the substances included in the subject corresponding to the arbitrary pixel by referring to the first table and the second table, with respect to the average value of pixel values of the arbitrary pixel calculated by the first calculating unit and the average value of the radiation quantum energy of the arbitrary pixel calculated by the second calculating unit.

2. The radiation imaging system according to claim 1, wherein the image processing unit further includes a pixel value generation unit configured to generate pixel values of the substances in accordance with the estimated information on the thicknesses of the substances and the mix ratio.

3. The radiation imaging system according to claim 2, wherein the pixel value generation unit includes a first pixel value generation unit configured to generate a first pixel value which is a pixel value of a first constitutive substance based on first information on a thickness of the first constitutive substance and the mix ratio and includes a second pixel value generation unit configured to generate a second pixel value which is a pixel value of a second constitutive substance based on second information on a thickness of the second constitutive substance and the mix ratio.

4. The radiation imaging system according to claim 3, wherein, when a linear attenuation coefficient obtained when radiation energy of the first constitutive substance in the two different substances included in the subject is represented by "E[kev]" is denoted by "$\mu_1(E)$", a linear attenuation coefficient obtained when radiation energy of the second constitutive substance in the two substances is represented by "E[kev]" is denoted by "$\mu_2(E)$", a thickness of the subject is denoted by "d", a mix ratio of the first constitutive substance is denoted by "$\gamma$", an arbitrary coefficient for conversion of the energy into a pixel value is denoted by "$\beta$", the first pixel value is denoted by "$I_1$", and the second pixel value is denoted by "$I_2$", the pixel value generation unit generates a pixel value of at least one of the substances by performing at least one of the following calculations:

$$I_1 = \beta \int_0^\infty n(E) e^{-\mu_1(E) d\gamma} E \, dE \text{ and}$$

$$I_2 = \beta \int_0^\infty n(E) e^{-\mu_2(E) d(1-\gamma)} E \, dE.$$

5. The radiation imaging system according to claim 3, wherein, when effective energy of the radiation is denoted by "$E_{\mathit{eff}}$", a linear attenuation coefficient obtained when effective energy of the radiation of the first constitutive substance in the two different substances included in the subject is represented by "$E_{\mathit{eff}}$[kev]" is denoted by "$\mu_1(E_{\mathit{eff}})$", a linear attenuation coefficient obtained when effective energy of the radiation of the second constitutive substance in the two substances is represented by "$E_{eff}$[kev]" is denoted by "$\mu_2(E_{eff})$", a thickness of the first constitutive substance is denoted by "$d_1$", a thickness of the second constitutive substance is denoted by "$d_2$", a mix ratio of the first substance is denoted by "$\gamma$", an arbitrary coefficient for conversion of the energy into a pixel value is denoted by "$\beta$", the first pixel value is denoted by "$I_1$", and the second pixel value is denoted by "$I_2$", the pixel value generation unit generates a pixel value of at least one of the substances by performing at least one of the following calculations:

$I_1 = \beta e^{-\mu_1(E_{eff})d_1\gamma}$ and $I_2 = \beta e^{-\mu_2(E_{eff})d_2(1-\gamma)}$.

6. The radiation imaging system according to claim 3, wherein, when effective energy of the radiation is denoted by "$E_{eff}$", a linear attenuation coefficient obtained when effective energy of the radiation of the first constitutive substance in the two different substances included in the subject is represented by "$E_{eff}$[kev]" is denoted by "$\mu_1(E_{eff})$", a linear attenuation coefficient obtained when effective energy of the radiation of the second constitutive substance in the two substances is represented by "$E_{eff}$[kev]" is denoted by "$\mu_2(E_{eff})$", a thickness of the subject is denoted by "$d$", a mix ratio of the first substance is denoted by "$\gamma$", an arbitrary coefficient for conversion of the energy into a pixel value is denoted by "$\beta$", a calculated arithmetic average of the pixel values of the arbitrary pixel is denoted by "$I_{Ave}$", the first pixel value is denoted by "$I_1$", and the second pixel value is denoted by "$I_2$", the pixel value generation unit generates a pixel value of at least one of the substances by performing at least one of the following calculations:

$I_1 = Ln(I_{Ave}) \dfrac{\mu_1(E_{eff})d\gamma}{\mu_1(E_{eff})d\gamma + \mu_2(E_{eff})d(1-\gamma)}$ and $I_2 = Ln(I_{Ave}) \dfrac{\mu_2(E_{eff})d(1-\gamma)}{\mu_1(E_{eff})d + \mu_2(E_{eff})d(1-\gamma)}$.

7. The radiation imaging system according to claim 2, wherein, when a linear attenuation coefficient obtained when radiation energy of the first constitutive substance in the two different substances included in the subject is represented by "E[kev]" is denoted by "$\mu_1(E)$", a linear attenuation coefficient obtained when radiation energy of the second constitutive substance in the two substances is represented by "E[kev]" is denoted by "$\mu_2(E)$", a thickness of the subject is denoted by "$d$", a mix ratio of the first constitutive substance is denoted by "$\gamma$", an arbitrary coefficient for conversion of the energy into a pixel value is denoted by "$\mu$", arbitrary monochromatic radiation energy is denoted by "$E_{mono}$", and a pixel value of energy having an arbitrary spectrum is denoted by "$I(E_{mono})$", the pixel value generation unit generates the pixel value of the energy having the arbitrary spectrum by performing the following calculation:

$I(E_{mono}) = \beta e^{-\mu_1(E_{mono})d_1\gamma - \mu_2(E_{mono})d_2(1-\gamma)}$.

8. The radiation imaging system according to claim 1, wherein
the estimation unit estimates information on the thicknesses and the mixing ratio of the subject corresponding to the arbitrary pixel by referring to the first table and the second table, with respect to the average of the pixel values of the arbitrary pixels calculated by performing an operation using attenuation coefficients of the substances included in the subject calculated by the first calculating unit and the average value of the radiation quantum energy of the arbitrary pixel calculated by the second calculating unit estimated by performing a calculation using the attenuation coefficients of the substances included in the subject, the first table, and the second table.

9. The radiation imaging system according to claim 8, wherein
the first table indicates the relationship among the estimated average of the pixel values of the arbitrary pixel, the thicknesses of the substances included in the subject, and densities of the substances included in the subject,
the second table indicates the relationship among the estimated average value of the radiation quantum energy of the arbitrary pixel, the thicknesses of the substances included in the subject, and the densities of the substances included in the subject, and
the estimation unit estimates information on the thicknesses and the densities of the substances included in the subject.

10. The radiation imaging system according to claim 9, wherein the image processing unit further includes a pixel value generation unit configured to generate pixel values of the substances in accordance with the estimated information on the thicknesses and the densities of the substances.

11. The radiation imaging system according to claim 1, wherein the average value of the radiation quantum energy is calculated using an amount of temporal and/or spatial change of a pixel value of the arbitrary pixel.

12. The radiation imaging system according to claim 1, wherein the first calculation unit calculates the average value of the pixel values from pixel values obtained in time series from the arbitrary pixel.

13. The radiation imaging system according to claim 1, wherein the first calculation unit calculates the average value of the pixel values from pixel values acquired from pixels around the arbitrary pixel.

* * * * *